(12) United States Patent
Nicholson et al.

(10) Patent No.: US 6,867,603 B2
(45) Date of Patent: Mar. 15, 2005

(54) METHOD FOR MEASURING HIGH FREQUENCY RESISTANCE IN DIESEL ENGINE LUBRICATION OIL

(75) Inventors: Warren Baxter Nicholson, El Paso, TX (US); Yingjie Lin, El Paso, TX (US); Larry M. Oberdier, Royal Oak, MI (US); Joseph Pierre Heremans, Troy, MI (US)

(73) Assignee: Delphi Technologies, Inc., Troy, MI (US)

( * ) Notice: Subject to any disclaimer, the term of this patent is extended or adjusted under 35 U.S.C. 154(b) by 42 days.

(21) Appl. No.: 10/310,126

(22) Filed: Dec. 4, 2002

(65) Prior Publication Data

US 2004/0108859 A1 Jun. 10, 2004

(51) Int. Cl.[7] .................. G01R 27/08; G01R 27/26
(52) U.S. Cl. .................. 324/698; 324/708; 324/709; 324/686
(58) Field of Search ................. 324/698, 553, 324/655, 668, 675, 682, 708, 709, 686; 123/196 R, 196 S, 198 D; 73/1.02, 53.05

(56) References Cited

U.S. PATENT DOCUMENTS

| | | | |
|---|---|---|---|
| 3,746,974 A | * | 7/1973 | Stoakes et al. ............ 324/686 |
| 4,926,120 A | * | 5/1990 | Veronesi et al. ............ 324/204 |
| 6,028,433 A | | 2/2000 | Cheiky-Zelina et al. .... 324/663 |
| 6,469,521 B1 | | 10/2002 | Klun et al. ................. 324/658 |
| 6,508,100 B2 | | 1/2003 | Berndorfer .................. 73/1.02 |
| 6,509,749 B1 | | 1/2003 | Buelna et al. .............. 324/698 |
| 6,535,001 B1 | | 3/2003 | Wang ......................... 324/698 |
| 6,557,396 B2 | | 5/2003 | Ismail et al. ............... 73/53.05 |
| 6,564,126 B1 | | 5/2003 | Lin et al. ...................... 701/30 |

FOREIGN PATENT DOCUMENTS

WO           98/46985        10/1998

* cited by examiner

*Primary Examiner*—Anjan K. Deb
(74) *Attorney, Agent, or Firm*—Jimmy L. Funke

(57) ABSTRACT

Soot content in Diesel engine lubrication oil is determined using electrical resistance measurements of the oil at high frequency. A sensor in the form of a capacitor is immersed in the oil, wherein the oil serves as a dielectric between the plates. The capacitance and resistance between the plates change as a function of engine oil condition. An inductor is placed in series with the sensor, and high frequencies are swept over a range to find resonance where the capacitive and inductive reactances cancel. At this frequency, the resistance of the oil is measured and the condition of the oil thereby determined.

8 Claims, 3 Drawing Sheets

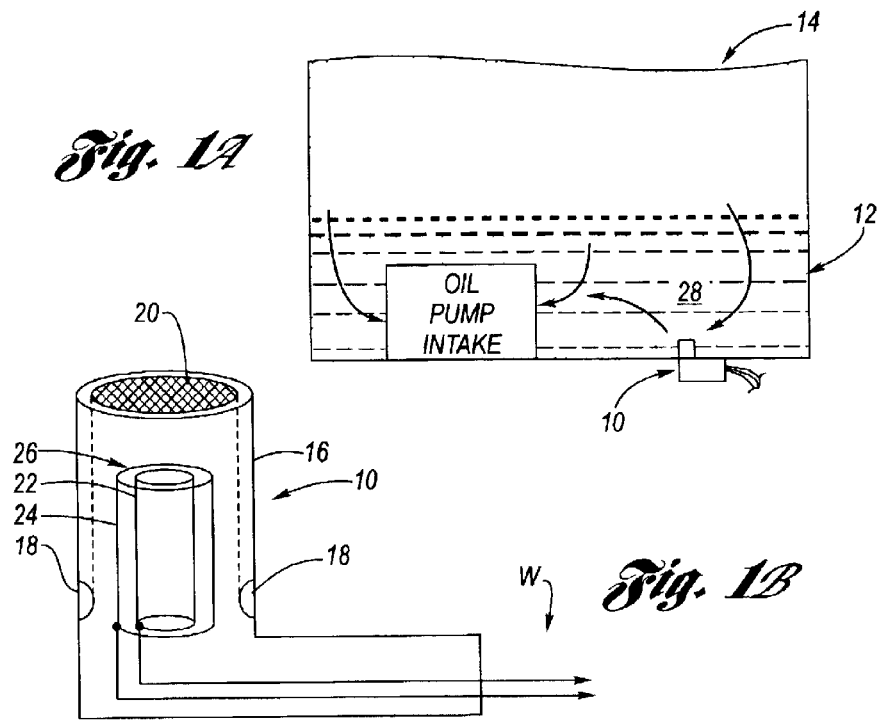
Fig. 1A
Fig. 1B
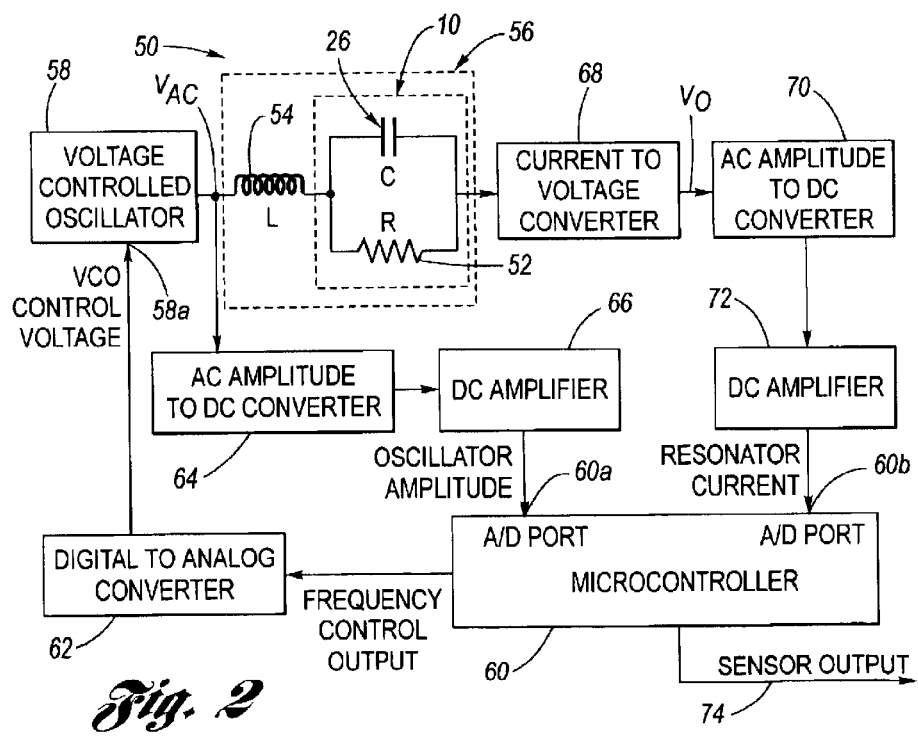
Fig. 2

METHOD FOR MEASURING HIGH FREQUENCY RESISTANCE IN DIESEL ENGINE LUBRICATION OIL

TECHNICAL FIELD

The present invention relates generally to Diesel engine oil contaminant sensors, and more particularly to a method for determining contamination of Diesel engine lubrication oil by measuring the resistance thereof at high frequency.

BACKGROUND OF THE INVENTION

When engine oils become contaminated with the by-products of combustion, their value as a lubricant is greatly diminished. The main contaminate in engine oils during normal combustion is carbon. Diesel engines produce large amounts of carbon, referred to as soot, during combustion and the measurement of the percentage of soot in the diesel oil gives an indication of when the oil should be changed.

Measurement attempts at DC and low frequency AC (ie., below about 1 kilo Hz) fail because the change in conductivity is very small for large changes in the percentages of soot. At high frequencies (ie., in the mega Hz range) the resistive losses due to the soot are measurable even at levels of less than one percent soot. The problem with the high frequency loss measurement is that the sensor, which defines a measurement volume, is a capacitor. Since the sensor has a capacitance associated with its physical shape, there is also a capacitive reactance associated with the sensor. The problem is the capacitive reactance is very low at these high frequencies (ie., on the order of between 1 to 6 hundred Ohms), and the resistance of the soot in oil which is in parallel with the capacitive reactance, is very high (ie., on the order of mega Ohms). There are methods that are used in a laboratory that can make the measurement, but the equipment is expensive and the setup must be nearly ideal (very short leads). The use of a network analyzer or vector voltmeter would be cost prohibitive, and an RF bridge measurement could be used if the resistance and capacitive reactance were near the same values. Thus, such a measurement is very difficult in the real world environment of an operating engine.

Accordingly, what remains needed in the art is a method, applicable to real world engine operation environments, for determining contamination of Diesel engine lubrication oil by measuring the resistance thereof at high frequency.

SUMMARY OF THE INVENTION

The soot content in Diesel engine lubrication oil is determined using electrical resistance measurements of the Diesel oil at high frequency which is independent of the brand of oil and immune to the effects of adding fresh oil with different dielectric or electrical properties than the original oil. "High frequency" is defined to be above about 2 mega Hz (for example, up to about 10 GHz).

A sensor is provided which is immersed in the lubricating oil of a Diesel engine, such as at the bottom of the crankcase. The sensor is in the form of a capacitor with either parallel plates or concentric tubes defining a measurement volume (tubes and plates being referred to hereinafter simply as "plates"). The lubricating oil provides a high dielectric constant between the plates which form the capacitor. As carbon contaminates build up in the oil, the capacitor behaves like a capacitor with a resistor in parallel. The oil resistance across the plates due to the carbon contaminates is very high (ie., in the mega Ohm range). But, the capacitive reactance in the mega Hz frequency range is low (ie., on the order of hundreds of Ohms). Thus, in order to ascertain the oil resistance, the capacitive reactance must be cancelled.

The present invention utilizes an inductor in series with the capacitor to thereby provide a resonant circuit. At resonance, the capacitive and inductive reactance vectors mutually cancel, leaving only the resistive component. In this regard, it is well known that at resonance the phase vectors of the capacitive reactance and inductive reactance mutually cancel, leaving just the resistive value. It is also known that the dielectric constant of different oils varies, and also the dielectric constant of any one oil changes as the additives are used up or breakdown. This means that while the inductance value remains constant, the capacitance value of the sensing element will be different with different oils and will change with time, and therefore, the resonate frequency will also change. Since the range of dielectric constants is known, the range of capacitance is also known, as is the frequency range, wherein a voltage controlled oscillator (VCO) is provided that will cover the range of frequencies due to dielectric change.

In a first preferred form of the invention, a microcontroller outputs a stream of bit patterns to a digital to analog converter (D/A converter) which outputs a changing, ramp like, analog voltage. The analog voltage ramp is connected to the VCO control input. The output of the VCO is a sweep of frequencies over the range of interest. The output of the VCO is connected to the resonant circuit. As the microcontroller sweeps the frequency into the resonate circuit, the voltage signal proportional to the resonate circuit current is checked for a maximum value, because at resonance the current is at a maximum. The microcontroller stores the peak current and the voltage amplitude of the excitation and then calculates the relative resistance of the oil. The microcontroller then outputs a signal in a format that is required by external electronics.

In a second, most preferred form of the invention, a phase locked loop (PLL) integrated circuit is utilized. The voltage controlled oscillator (VCO) within the PLL is set to free-run at a frequency that is in the range of frequencies expected due to the change of dielectric constant of the oil within the sensor. When phase information is presented to the PLL inputs, an internal error signal is generated if an out of phase condition exists. This error signal is filtered and connected to the VCO control pin, which changes the VCO frequency until the signals are in phase, at which time the PLL is locked and resoance is achieved. A current to voltage converter provides an output whereby the current at resonance may be determined. The VCO output is a constant amplitude square wave, thereby enabling the selection of a convenient drive voltage level for the resonant circuit by which the relative resistive loss introduced by the soot in the oil may be calculated, using the current at resonance, by the microcontroller and output in a form that is required by external electronics.

Accordingly, it is an object of the present invention to measure the electrical resistance of Diesel engine lubrication oil at high frequency to thereby determine the amount of soot therein, wherein the measurement is independent of the brand of oil and immune to the effects of adding fresh oil with different dielectric or electrical properties than the original oil.

This and additional objects, features and advantages of the present invention will become clearer from the following specification of a preferred embodiment.

BRIEF DESCRIPTION OF THE DRAWINGS

FIG. 1A depicts the engine placement of an oil sensor for resistance measurements according to the present invention.

FIG. 1B depicts a detail view of the oil sensor of FIG. 1.

FIG. 2 is a first example of an electrical circuit to measure resistance of Diesel engine lubrication oil at high frequencies.

DESCRIPTION OF THE PREFERRED EMBODIMENT

Figure 3:
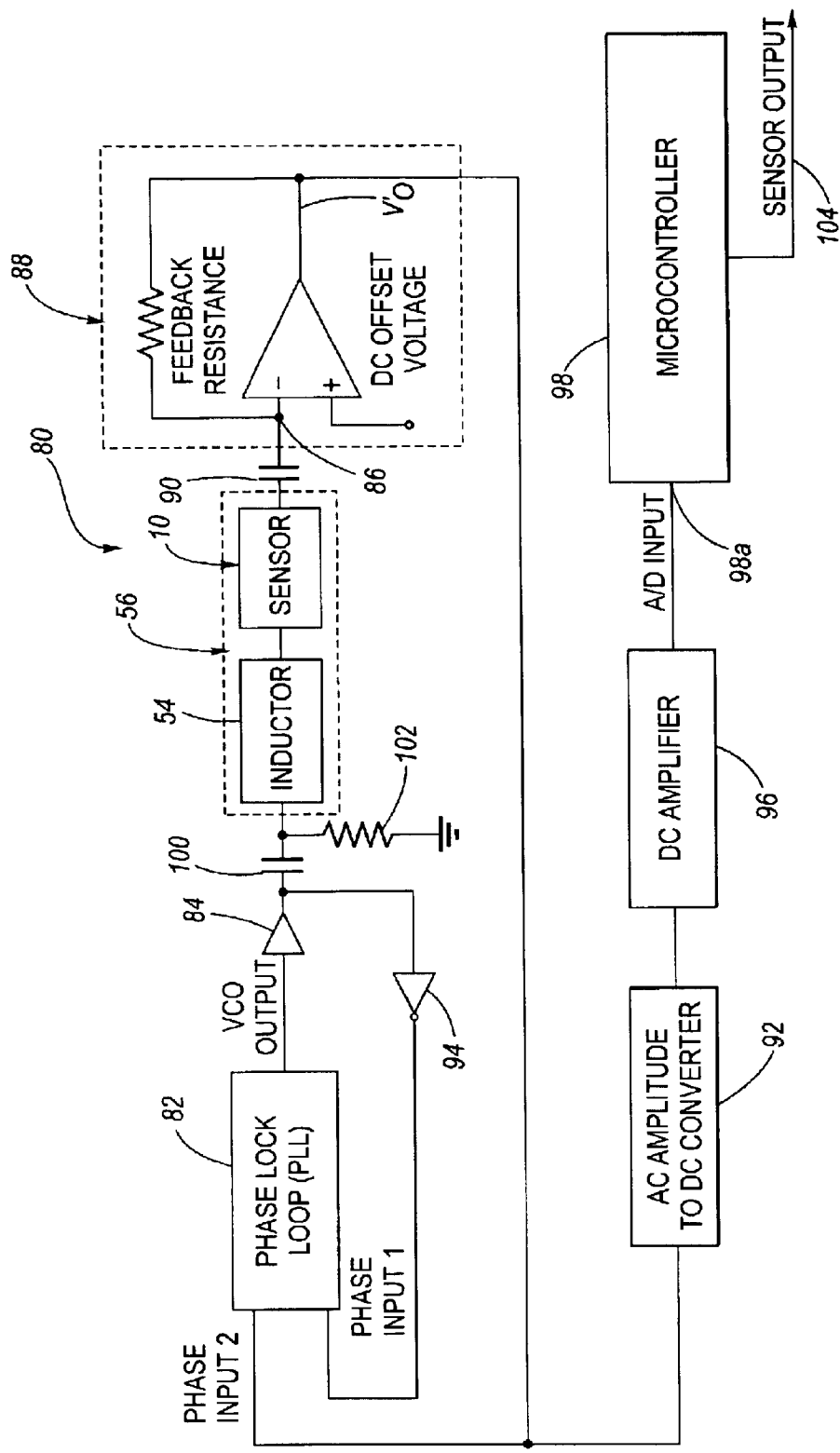
FIG. 3 is a second example of an electrical circuit to measure resistance of Diesel engine lubrication oil at high frequencies.

Referring now to the Drawing, FIG. 1A depicts an environment of placement and operation of a Diesel engine lubrication oil condition sensor 10. The sensor 10 is located at the bottom of an oil pan 12 of a Diesel engine 14. As shown at FIG. 1B, the oil sensor 10 has a cylindrical shell 16 having apertures 18 and an open top end 20. Inside the shell 16 is a pair of concentrically arranged and mutually separated cylindrical capacitor plates 22, 24 which collectively form a capacitor 26, each of which being connected to a respective portion of wiring, W.

In operation of the sensor 10, which sensor construction is known in the prior art, oil 28 in the oil pan 12 is sloshed, causing the oil to flowably fill the space separating the plates 22, 24. As a result, the capacitance C and the resistance R (see FIG. 2) of the space between the plates 22,24 changes over time as the condition of the oil changes with hours of operation of the Diesel engine.

FIG. 2 is a first example of an electrical circuit 50 to measure resistance of Diesel engine lubrication oil at high frequencies utilizing a series resonant LC circuit. The sensor 10 is modeled as the aforesaid capacitor 26 having a capacitance C with a resistor 52 have a resistance R in parallel therewith, wherein I/R represents the conductance of the physical configuration of the metal plates of the sensor 10 filled with Diesel engine lubrication oil to be measured, and wherein C represents the capacitance of the physical configuration of the metal plates (22, 24 of FIG. 1B) of the sensor 10 filled with the oil. An inductor 54 having an inductance L is chosen in accordance with the dimensions of the sensor 10 to provide an LC series resonant circuit 56 having resonance over a predetermined frequency range, for example between 2 MHz and 3 MHz.

The Diesel engine lubrication oil provides a high dielectric constant for the capacitor 26. As carbon contaminates (soot) build up in the oil, the capacitor 26 behaves like a capacitance C with a resistance R in parallel therewith. The resistance R due to the carbon contaminates is very high (ie., in the mega Ohm range), and the capacitive reactance of the capacitor 26 in the mega Hz frequency range is low (ie., on the order of hundreds of Ohms).

It is well known in the art that at resonance the phase vectors of the capacitive reactance and inductive reactance cancel, leaving only a resistive value. It is also known that the dielectric constant of different Diesel engine oils varies, and also the dielectric constant of any one oil changes as the additives are used up or breakdown. This means the capacitance C of the sensor 10 will be different with different oils and will change with time and, therefore, the resonant frequency will also change. Since the range of dielectric constants is known, the range of capacitance C is also known, as is the frequency range over which resonance will occur. Thus, a voltage controlled oscillator (VCO) 58 of the electrical circuit 50 is preselected to cover the predetermined range of frequencies over which resonance of the resonant circuit 56 will occur due to changes of the dielectric constant of the capacitor 26.

In FIG. 2, a microcontroller 60 outputs a stream of bit patterns to a digital to analog converter (D/A converter) 62 which outputs a changing, ramp like, analog voltage. The analog voltage ramp is connected to a control input 58a of the VCO 58. The output of the VCO 58 is a sweep of frequencies over the range of interest for providing resonance. The output of the VCO 58 is connected to the resonant circuit 56 and to an AC amplitude to DC converter 64. The DC output of the AC amplitude to DC converter 64 is amplified by a DC Amplifier 66 and connected to an A/D input port 60a of the microcontroller 60 which monitors the AC voltage level $V_{AC}$ being fed into the resonant circuit 56. The resonant circuit 56 consists of the aforementioned LC series resonant circuit 56, comprising the inductor 54, having a fixed inductance L, and the sensor 10, wherein the sensor includes the capacitor 26 having a changing capacitance C and the resistor 52 having a changing resistance R in parallel therewith, the changing values of capacitance and resistance being related to the condition of the oil.

Figure 4:
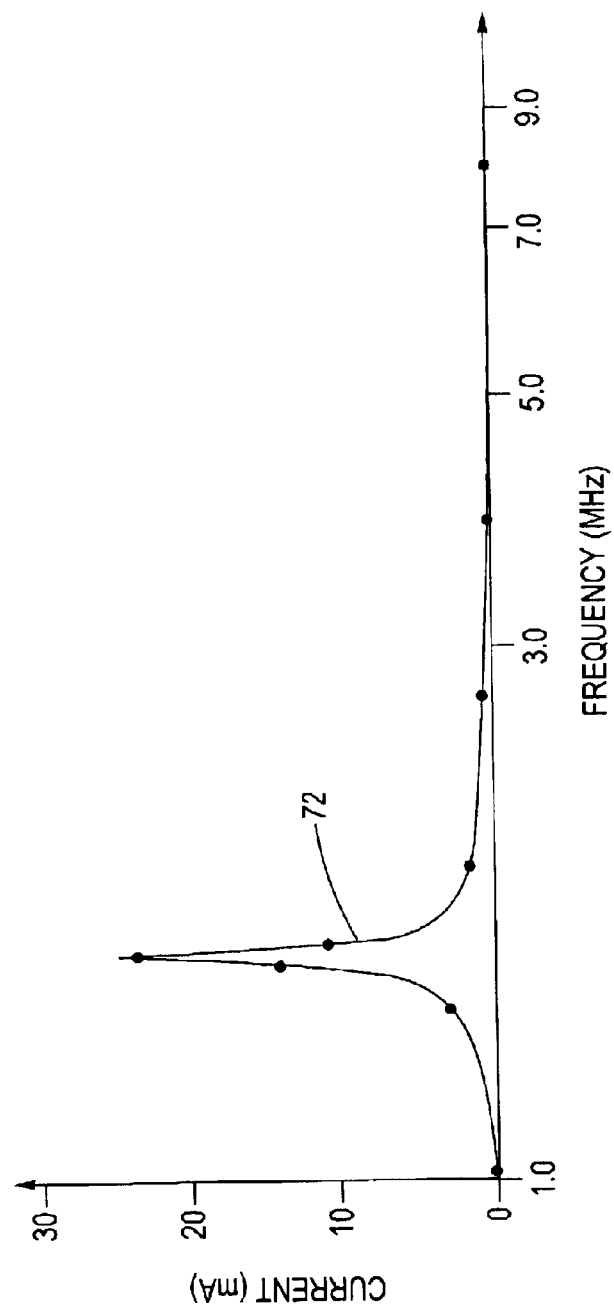
FIG. 4 shows a computer simulation that graphs the current increase at resonance of an electrical circuit of FIG. 2 or 3.

The output of the resonant circuit 56 is connected to a current to voltage converter 68 which converts the currents flowing in the resonant circuit to a proportional AC voltage output $V_O$. The output of the current to voltage converter 68 is connected to an AC amplitude to DC converter 70 whose output is amplified by DC Amplifier 72 and connected to an A/D input port 60b of the microcontroller 60 which monitors the AC voltage level $V_O$. As the microcontroller 60 varies the input control voltage to the VCO 58, the VCO output frequency is swept into the resonant circuit 56. $V_O$ is monitored by the microprocessor 60 at the A/D port 60b until a maximum voltage is detected. At this maximum voltage, the VCO output is at the resonant frequency of resonant circuit 56, and the current is at a maximum. In this regard, FIG. 4 shows a computer simulation plot 72 of how the current increases at resonance.

The microcontroller 60 stores the maximum (peak) current and the voltage amplitude and then calculates the relative resistance of the oil. The microcontroller 60 then outputs a signal 74 in a format that is required by external electronics. In this regard, the microcontroller 60 has incorporated within it all parameters, constants, algorithms, and programs to effect the operation of the circuit 50 and the present invention utilizing the conductivity or conductance by techniques well known in the art.

FIG. 3 is a second example of an electrical circuit 80, which is the most preferred method of the present invention to measure resistance of Diesel engine lubrication oil at high frequencies, wherein a phase locked loop (PLL) 82 integrated circuit is used in conjunction with the aforedescribed resonant circuit 56.

A voltage controlled oscillator (VCO) incorporated within the PLL 82 is set to free-run at a frequency that is in the range of frequencies expected due to the change of dielectric constant of the oil within the sensor 10, as previously described in FIG. 2. The VCO output of PLL 82 is buffered by a Buffer 84 to provide the required drive current to the resonant circuit 56. The current flowing in the resonant circuit 56 is connected to the virtual ground input 86 of a current to voltage converter 88 through a DC blocking capacitor 90. The voltage output V'₀ of the current to voltage converter 88 is connected to the Phase Input 2 of the PLL 82 and to an AC amplitude to DC converter 92. The output of the Buffer 84 is inverted by a Phase Inverter 94 to account for the phase inversion in output V'₀ by the current to voltage converter 88, and is connected to Phase Input 1 of the PLL 82.

The phase of the voltage output V'₀ of the current to voltage converter 88 at Phase Input 2 of PLL 82 will lead or lag the VCO output of the PLL above or below resonance of the resonant circuit 56, and will only be in phase with the voltage at Phase Input 1 at resonance, due to the fact that at resonance, the resonant circuit 56 is purely resistive. In this regard, at resonance, the voltage across the resonant circuit 56, represented by the voltage at Phase Input 1 of the PLL 82, is in phase with the current through the resonant circuit represented by the voltage V'₀ at Phase Input 2 taking into account the phase shift produced by the current to voltage converter 88 and compensated for by the Phase Inverter 94.

When phase information is presented to the PLL 82 through input signals at Phase Input 1 and at Phase Input 2, an internal error signal is generated within the PLL if an out of phase condition exists. This error signal is filtered and connected to an internal VCO control pin, which changes the VCO frequency until the input signals at Phase Input 1 and at Phase Input 2 are in phase, at which time the PLL 82 locks, the VCO frequency does not change and resonance is present.

The output of the AC amplitude to DC converter 92 is fed to a DC Amplifier 96, the output of which is connected to an A/D input 98a of a microcontroller 98. A capacitor 100 serves as a DC blocking capacitor and passes the high frequencies from the VCO output of the PLL 82 and the Buffer 84 to the resonant circuit 56. A resistance 102 establishes a ground reference for the high frequency AC voltage passed by the capacitor 100. The VCO output of the PLL 82 is a constant amplitude square wave, thereby providing a constant voltage to the resonant circuit 56.

A convenient voltage amplitude can be selected for calculation by the microcontroller 98 along with the measured current of the resonant circuit 58 at resonance, represented by the voltage at the A/D input 98 of the microcontroller. The microcontroller 98 then calculates the relative resistive loss introduced by the soot in the oil, and thereupon outputs a signal 104 in a format required, by for example, an "Engine Management System," that is related to the percentage of soot in the Diesel engine oil.

The time required for the PLL 82 to achieve lock (resonance) is relatively short, for example, one millisecond. Hence, with a proper delay incorporated into the microcontroller 98 after being powered on, the voltage at the A/D input 98a of the microcontroller represents the current of the resonant circuit 56 at resonance. Having selected a convenient voltage amplitude for calculation by the microcontroller 98, as described above, the microcontroller can calculate the resistance R of the sensor 10 due to the condition of the oil.

As is known in the art, as the Diesel engine lubrication oil becomes contaminated with soot, the resistance decreases as a linear function of soot concentration, whereby the resistance R is greatest with fresh, clean (ie., soot free) Diesel engine lubrication oil. With fresh, clean Diesel engine lubrication oil in a vehicle, and with a proper delay incorporated into microcontroller 98 after being powered on, the resistance R is calculated and used as a reference resistance. Later calculated resistances are compared to this reference resistance by which the soot concentration may be ascertained.

The microcontroller 98 has incorporated within it all parameters, constants, algorithms, and programs to effect the operation of the circuit 80 and the present invention utilizing the conductivity ratio and conductivity or conductance by techniques well known in the art.

To those skilled in the art to which this invention appertains, the above described preferred embodiment may be subject to change or modification. Such change or modification can be carried out without departing from the scope of the invention, which is intended to be limited only by the scope of the appended claims.

What is claimed is:

1. A method for measuring high frequency resistance in Diesel engine lubrication oil, comprising the steps of:

immersing a capacitor in the oil such that the oil provides a dielectric between the plates thereof, wherein the oil acts as a resistor between the plates;

connecting an inductor in series with the capacitor, wherein the capacitor and the inductor collectively provide a resonant circuit;

sweeping a predetermined range of high frequency voltage through the resonant circuit;

sensing resonance of the resonant circuit, whereat an inductive reactance of the inductor equals and is opposite to a capacitive reactance of the capacitor at a frequency within said predetermined range; and determining resistance of the oil between the plates of the capacitor at the frequency.

2. The method of claim 1, further comprising determining an oil condition of the oil responsive to the resistance.

3. The method of claim 1, wherein said steps of sensing and determining further comprise:

sensing a peak current value and a drive voltage value over the predetermined range of frequencies;

storing a peak current value;

storing a drive voltage value; and determining the resistance of the oil using the stored peak current and voltage values.

4. The method of claim 3, further comprising determining an oil condition of the oil responsive to the resistance.

5. The method of claim 1, wherein said step of sensing and determining further comprise:

sensing difference of phase between current and voltage over the predetermined range of frequencies; and determining the resistance of the oil when the difference equals zero.

6. The method of claim 5, further comprising determining an oil condition of the oil responsive to the resistance.

7. A method for measuring high frequency resistance in Diesel engine lubrication oil, comprising the steps of:

immersing a capacitor in the oil such that the oil provides a dielectric between the plates thereof, wherein the oil acts as a resistor between the plates;

connecting an inductor in series with the capacitor, wherein the capacitor and the inductor collectively provide a resonant circuit;

sweeping a predetermined range of high frequency voltage through the resonant circuit;

sensing resonance of the resonant circuit, whereat an inductive reactance of the inductor equals and is opposite to a capacitive reactance of the capacitor at a frequency within said predetermined range, wherein said step of sensing comprises:

sensing a peak current value and a drive voltage value over the predetermined range of frequencies;

storing a peak current value; and storing a drive voltage value;

determining resistance of the oil between the plates using the stored peak current and voltage values; and determining an oil condition of the oil responsive to the resistance.

8. A method for measuring high frequency resistance in Diesel engine lubrication oil, comprising the steps of:

immersing a capacitor in the oil such that the oil provides a dielectric between the plates thereof, wherein the oil acts as a resistor between the plates;

connecting an inductor in series with the capacitor, wherein the capacitor and the inductor collectively provides a resonant circuit;

sweeping a predetermined range of high frequency voltage through the resonant circuit;

sensing resonance of the resonant circuit, whereat an inductive reactance of the inductor equals and is opposite to a capacitive reactance of the capacitor at a frequency within said predetermined range, wherein said step of sensing comprises sensing difference of phase between current and voltage over the predetermined range of frequencies;

determining resistance of the oil between the plates when the difference equals zero; and determining an oil condition of the oil responsive to the resistance.

* * * * *